United States Patent
Goto et al.

(10) Patent No.: US 6,844,372 B2
(45) Date of Patent: Jan. 18, 2005

(54) CROSSLINKED ANION-EXCHANGE RESIN OR SALT THEREOF AND PHOSPHORUS ADSORBENT COMPRISING THE SAME

(75) Inventors: Takeshi Goto, Tsukuba (JP); Kazuhisa Yoshitake, Tsukuba (JP); Kazuteru Moriyama, Tsukuba (JP); Shuichi Toriya, Suita (JP); Tsutomu Yuasa, Osaka (JP); Hideyuki Nishibayashi, Kobe (JP)

(73) Assignee: Hisamitsu Pharmaceutical Co., Inc., Saga (JP)

(*) Notice: Subject to any disclaimer, the term of this patent is extended or adjusted under 35 U.S.C. 154(b) by 0 days.

(21) Appl. No.: 10/220,781

(22) PCT Filed: Mar. 9, 2001

(86) PCT No.: PCT/JP01/01852

§ 371 (c)(1),
(2), (4) Date: Nov. 18, 2002

(87) PCT Pub. No.: WO01/66607

PCT Pub. Date: Sep. 13, 2001

(65) Prior Publication Data

US 2003/0092782 A1 May 15, 2003

(30) Foreign Application Priority Data

Mar. 9, 2000 (JP) .................................. 2000-065494

(51) Int. Cl.⁷ .................................................. C08F 8/00
(52) U.S. Cl. ........................ 521/31; 521/25; 424/78.1; 424/78.12; 424/78.14
(58) Field of Search .................. 521/25, 31; 424/78.1, 424/78.12, 78.14

(56) References Cited

U.S. PATENT DOCUMENTS 4,071,478 A * 1/1978 Shen et al. .................. 260/2 R

FOREIGN PATENT DOCUMENTS

| EP | 793960 | 9/1997 |
| JP | 2000-143798 | 5/2000 |
| WO | 94/19379 | 9/1994 |
| WO | 95/05184 | 2/1995 |
| WO | 96/25440 | 8/1996 |
| WO | 96/39156 | 12/1996 |
| WO | 98/03185 | 1/1998 |

OTHER PUBLICATIONS

English Language translation of Laid–open Kokai Patent JP2000–143798–A, published May 26, 2000.*

* cited by examiner

*Primary Examiner*—Fred Teskin
(74) *Attorney, Agent, or Firm*—Wenderoth, Lind & Ponack, L.L.P.

(57) ABSTRACT

An cross-linked anion exchange resin or a salt thereof obtained by reacting a polymer (A) having amino and/or imino groups in the total number of two or more per molecule with a compound (B) having two or more functional groups capable of reacting with amino and/or imino group contained in the polymer (A). The resin or salt has a water absorption ratio of 4.0 or lower.

8 Claims, 6 Drawing Sheets

CROSSLINKED ANION-EXCHANGE RESIN OR SALT THEREOF AND PHOSPHORUS ADSORBENT COMPRISING THE SAME

Crosslinked anion exchange resin or salt thereof and phosphorus adsorbent comprising the same.

TECHNICAL FIELD

The present invention relates to a crosslinked anion exchange resin or a salt thereof which is crosslinked to an optimal degree of crosslinking by a compound having two or more functional groups capable of reacting to amino or imino groups. The crosslinked anion exchange resin has the optimal degree of crosslinking and thus a high adsorption capacity with respect to phosphorus compounds such as phosphates, and can be used as a phosphorus adsorbent for use in purification of water in lakes, lagoons, rivers, or the like, or as a preventive and/or therapeutic agent of hyperphosphatemia for use in medical treatment.

BACKGROUND ART

It is known that a patient with renal dysfunction gradually loses a capability to excrete the body's phosphorus into urine due to a decline in renal functions associated with a deterioration of the renal lesion and results in hyperphosphatemia. In patients who suffer from the condition of hyperphosphatemia for an extended period, phosphorus accumulated in the body induces various hazards such as a decrease in serum calcium, and thus medical treatment of hyperphosphatemia was indispensable for the patients.

For the treatment of hyperphosphatemia, a therapy by oral administration of a phosphorus adsorbent has been practiced as well as the dietetic therapy. The therapy by oral administration of a phosphorus adsorbent is based on a function of the phosphorus adsorbent to adsorb and trap phosphate ions present in food ingested by the patient, thus suppressing intake and accumulation of phosphorus in the body and consequently reducing phosphorus concentration in blood. Currently, three kinds of medicines, aluminum preparations, calcium preparations and magnesium preparations, are mainly used as the oral phosphorus adsorbent. But since the medicines are necessarily administrated for a prolonged term for those patients with renal failure, the aluminum preparations containing aluminum hydroxide raise a problem of adverse reactions such as aluminum encephalopathy and aluminum osteopathy induced by the uptake of aluminum into the patient body. Additionally, the calcium preparations (calcium carbonate, calcium acetate) have the similar problem since they have lower phosphorus adsorption capacities compared to the aluminum preparations, demanding an increased administration of the medicine and consequently resulting in an uptake of more calcium possibly leading to hypercalcemia. Moreover, the magnesium preparations (magnesium carbonate) have a problem of hypermagnesemia, as with the calcium preparations.

In view of the problems associated with the conventional oral phosphorus adsorbents for medicine, recently, methods to use an anion exchange resin as the phosphorus adsorbent have been studied. For example, Japanese PCT International Publication No. 9-504782 (WO95/05184) discloses that an anion exchange resin of polyallylamine hydrochloride crosslinked with epichlorohydrin can be used as a medicinal phosphoric acid adsorbent. Additionally, in Japanese Unexamined Patent Publication No. 9-295941 was disclosed that 2-methylimidazole-epichlorohydrin copolymer, cholestyramine and the like that were used as bile acid adsorbents can also be used as medicinal phosphorus adsorbents, and in Japanese PCT International Publication No. 8-506846 (WO96/25440) that an anion exchange resin having guanitidyl (sic) groups may adsorb phosphoric acid.

Although these anion exchange resins exhibit sufficient adsorption capacities with respect to phosphate ion, there were some resins that should be administered in a greater amount to raise the therapeutic effect. Additionally, according to a survey in the U.S., about 25% of the renal failure patients were concurrently suffering from hyperlipemia, while the remaining 75% patients were not required to decrease the blood cholesterol level. But among the conventional medicinal phosphorus adsorbents, there were some that adsorb not only phosphoric acid, but also organic acids including raw materials of cholesterol such as bile acids (e.g., glycocholic acid), and consequently induce the hazard of a decrease in the blood cholesterol level. Therefore, there was a need to raise both the phosphoric acid adsorption capacity and the phosphoric acid selectivity.

Thereupon, objects of the present invention are to find a crosslinked anion exchange resin that is excellent both in the phosphorus adsorption capacity and the selectivity to phosphorus, and to provide a phosphorus adsorbent comprising the crosslinked anion exchange resin or the salt thereof, by studying kinds of anion exchange resin and effects of crosslinking with crosslinking agents.

DISCLOSURE OF THE INVENTION

A crosslinked anion exchange resin or a salt thereof of the present invention features in that it is the crosslinked anion exchange resin or a salt thereof which is obtained by reacting a polymer (A) having amino and/or imino groups in the total number of two or more per molecule with a compound (B) having two or more functional groups capable of reacting with the amino and/or imino groups and has a water absorption ratio of 4.0 or less. It is because it was found that the polymer (A) with the compound (B) through two or more amino or imino groups above a specific crosslinking degree provided a crosslinked anion exchange resin excellent both in the phosphorus adsorption capacity and the selectivity to phosphorus. The crosslinked anion exchange resin has an excellent phosphorus adsorbing capacity also in a salt from such as hydrochloride. Meanwhile, the "amino or imino groups" in the polymer (A) of the present invention include a nitrogen atom of tert-amine, and the polymers (A) include polymers having the "amino or imino groups" above in the main chains and/or in the branched chains.

A crosslinked anion exchange resin or a salt thereof which is obtained by reacting a polymer (A) having amino and/or imino groups in the total number of two or more per molecule with a compound (B) having two or more functional groups capable of reacting with the amino and/or imino groups in the absence of a solvent or in the presence of an nonaqueous solvent is also embraced in the present invention.

DESCRIPTION OF THE PREFERRED EMBODIMENTS

As a consequence of intensive studies on the method for increasing the phosphorus adsorption capacity and the selectivity to phosphorus, the present inventors have found that it was possible to increase the phosphorus selectivity of an anion exchange resin by crosslinking the resin to a higher degree of crosslinking by using a greater amount of a crosslinking agent. Additionally, it was found that the amount of the crosslinking agent used in preparation had a good correlation with the water absorption ratio of the resulting resin, and that by setting an upper limit to the water absorption ratio, it was possible to prepare a crosslinked anion exchange resin or a salt thereof excellent in both the phosphorus adsorption capacity and the selectivity to phosphorus. Further, the inventors have also found that it was effective to conduct the crosslinking reaction in the absence of a solvent or in a presence of a nonaqueous solvent for obtaining the anion exchange resin for phosphorus adsorption having a water absorption ratio of 4.0 or less, and thus completed the present invention.

Namely in first aspect of the present invention, the crosslinked anion exchange resin or the salt thereof is characterized in that it is obtained by reacting a polymer (A) having amino and/or imino groups with a compound (B) having two or more functional groups capable of reacting with amino and/or imino groups, and has a water absorption ratio of 4.0 or less. Additionally in a second invention of the present invention, the crosslinked anion exchange resin or the salt thereof is characterized in that it is obtained in a reaction of polymer (A) having amino and/or imino groups and a compound (B) having two or more functional groups capable of reacting with the amino and/or imino groups in the absence of a solvent or in the presence of a nonaqueous solvent.

The polymer (A) has preferably a number averaged molecular weight of 200 or more. In a favorable embodiment of the present invention, the polymer (A) is at least one or more polymer selected from the group consisting of polyalkyleneimine, polyallylamine, polyvinylamine and allylamine-vinylamine copolymer. Meanwhile, an amine value of the polymer (A) is preferably 8 to 67 mg eq/g.

The phosphorus adsorbent comprising the crosslinked anion exchange resin and/or the salt thereof of the present invention may be used as a phosphorus adsorbent for purification of water in lakes, lagoons and rivers as well as of wastewater, and also as a phosphorus adsorbent for medicines. In particular, a medicine comprising the crosslinked anion exchange resin or the pharmaceutically acceptable salt thereof exerts a beneficial medicinal effect as a preventive and/or therapeutic agent of hyperphosphatemia.

The term, "polymer", according to the present invention is not intended to mean only a homopolymer, but also include copolymers that do not impede the present inventive object and multi-component copolymers consisting of three or more components. Hereinafter, the present invention will be described in detail.

The crosslinked anion exchange resin or the salt thereof of the present invention can be obtained from polymer (A) having amino or imino groups in the total number of two or more in a molecule. Namely, the polymer (A) is not limited so far as the polymer has two or more amino groups, two or more imino groups, or one or more amino or imino groups respectively in a molecule. It is because the amino and/or imino groups are the sites being crosslinked with the compound (B). Since the crosslinking may become insufficient when there is only one crosslinking site in a polymer molecule, a polymer having amino group and/or imino group in the total number of two or more is preferably selected as the polymer (A). Even after the crosslinking reaction, the polymer still has amino or imino groups that are not involved in the crosslinking reaction, and thus retains the anion exchange capacity.

Molecular weight of the polymer (A) above is not limited particularly, but preferably 200 or more as number averaged molecular weight. A polymer having the molecular weight of below 200 is not favorable since the polymer provides a fragile crosslinked anion exchange resin with an inferior strength. The lower limit of the molecular weight thereof is more preferably 500 or more as number averaged molecular weight. On the other hand, even though a polymer having a higher molecular weight is not particularly inconvenient, a polymer having an excessively high molecular weight may cause an entanglement of the polymer chains and thus affect the ion exchange property and the phosphorus adsorption property. Therefore, a polymer having a number averaged molecular weight of 10 million or less is recommended. The upper limit of the molecular weight is more preferably 1 million or less, more preferably 500 thousand or less, and most preferably 100 thousand or less.

As described above, the polymer (A) above has amino and/or imino groups in the total number of two or more. But since it is necessary to raise a degree of crosslinking by adding more crosslinking agent in the reaction mixture for obtaining a highly crosslinked polymer having a water absorption ratio of 4.0 or less, the polymer (A) has preferably more amino and/or imino groups where the crosslinking reaction possibly occurs. Therefore, polymers having alkyleneimine, vinylamine, or allylamine (including the salts thereof) as a main constitutional monomer, i.e., polyalkyleneimine, polyvinylamine, and polyallylamine, are most preferable. Of course, polymers comprising two or more polymers selected from alkyleneimine, vinylamine and allylamine may be also used, and a vinylamine-allylamine copolymer is most preferable. Additionally, modified resins (derivatives) prepared by reacting these amine polymers with ethylene oxide, glycidol or the like can also be used.

Meanwhile, as the polyalkyleneimine, polyethyleneimine and/or polyethylene-propyleneimine or the like can be most preferably used, and an alkyleneimine having an alkylene group of up to 8 carbons may also be used as a (co)monomer. Further, the polyethyleneimines are commercially available for example in trade name "EPOMIN SP" series from Nippon Shokubai Co., Ltd. (e.g., "EPOMIN SP-006", "EPOMIN SP-018", "EPOMIN SP-200", etc.), and these products may be used as the polymer (A) for the crosslinking.

Additionally, copolymers prepared by copolymerization of alkyleneimine, vinylamine, or allylamine with other monomers may also be used as the polymer (A). The other monomers that may be copolymerized are, for example, monomers containing amino group(s) such as dimethylaminoethyl(meth)acrylate, diethylaminoethyl (meth)acrylate, dimethylaminopropyl(meth)acrylate, diethylaminopropyl(meth)acrylate, 2-hydroxydimethylaminopropyl(meth)acrylate, aminoethyl (meth)acrylate, etc, or the salts thereof such as hydrochloride, hydrobromide, sulfate, nitrate, acetate, propionate, etc., [herein, "(meth)acrylate" means acrylate and methacrylate]; monomers containing amide group(s) such as (meth)acrylamide, t-butyl(meth)acrylamide, etc.; monomers containing hydroxyl group(s) such as hydroxyethyl(meth)acrylate, polyethyleneglycol mono (meth)acrylate, polyethyleneglycol monoisoprenolether, polyethyleneglycol monoallylether, hydroxypropyl(meth) acrylate, polypropyleneglycol mono(meth)acrylate, polypropyleneglycol monoisoprenolether, polypropyleneglycol monoallylether, α-hydroxy acrylic acid, N-methylol (meth)acrylamide, vinylalcohol, allylalcohol, 3-methyl-3-buten-1-ol (isoprenol), glycerol monoallylether, etc.; (meth) acrylates such as methyl(meth)acrylate, ethyl(meth)acrylate, etc.; or styrene, α-methylstyrene, vinyl acetate, vinylpyrrolidone, vinyl ethers, etc. Additionally, weak basic anion exchange resins known in the art containing amino or imino groups may also be used as the polymer (A).

A preferable range of the total amount of the amino and/or imino groups, defined by an amine value per gram of the polymer (A), is 8 to 67 mg eq/g. A polymer (A) having the amine value of smaller than 8 mg eq/g tends to yield a product insufficient in crosslinking. The more preferable lower limit of the amine value is 10 mg eq/g, and the upper limit is 25 mg eq/g. The amine value of the polymer (A) can be determined, for example, by neutralization titration in a nonaqueous solution. Concretely, the amine value can be determined by the following method.

(1) A solution of 0.5N p-toluenesulfonic acid in acetic acid (hereinafter, abbreviated as PTS) is prepared. About 0.3 g of sodium carbonate (purity: A mass %) is weighed (accurately to a 0.1 mg order) (sodium carbonate amount: M mg), and dissolved in 10 ml of methanol and 30 ml of acetic acid. The resulting solution is titrated with PTS, and a factor F of PTS is calculated from the titer ($V_1$ ml). The factor F of PTS is calculated by the following equation.

$$F=(M \times A)/(100 \times 105.99 \times 2 \times V_1).$$

(2) About 0.2 g of polymer (A) (resin solid content: N mass %) is weighed (accurately to a 0.1 mg order) (amount: S g), and dissolved in 10 ml of methanol. After 30 ml of acetic acid was added to the solution, the resulting solution was titrated with PTS above and the amine value of polymer (A) is calculated from the titer ($V_2$ ml). The amine value (mg eq/g) per g of the polymer (solid content) is calculated by the following equation by using the factor F of PTS obtained in (1).

$$\text{Amine value}=(0.5 \times F \times V_2)/(S \times N \times 10).$$

According to the present invention, a crosslinked anion exchange resin crosslinked so as to have a water absorption ratio of 4.0 or less is obtained by reacting a polymer (A) having amino and/or imino groups with a compound (B), used as a crosslinking agent, having two or more functional groups capable of reacting the amino or imino groups. Examples of the compound (B) include the following compounds.

(1) Compounds having vinyl groups capable of the Michael addition reaction and carboxylic ester groups; the vinyl groups capable of the Michael addition reaction accept nucleophilic additions of amino or an imino groups in the polymer (A), making the polymer (A) and the compound (B) bind to each other (Michael addition-type reaction). Additionally, since the carboxylic ester groups of the compound (B) also react with other amino and/or imino groups forming amide bonds, a reaction between the compound (B) with amino and/or imino groups in different molecules of the polymer (A) yields a crosslinked polymer in which molecules of the polymer (A) are crosslinked with the compound (B).

Concretely, favorable examples of the compound (B) are (meth)acrylic esters, fumaric mono- or diesters, maleic mono- or diesters, itaconic mono- or diesters and so on, respectively having ester groups such as alkylesters, having 1 to 10 carbons, cycloalkylesters, benzylesters, etc. Methyl acrylate is most favorable among the examples above in view of the succeeding processes necessary to remove alcohol released upon formation of the amide bonds and of the phosphorus adsorption capacity per weight of the resulting phosphorus adsorbent.

(2) Epihalohydrins; when the amino or imino groups in the polymer (A) are present in an inorganic salt form, epihalohydrins form a bisammonium salt therewith and make the polymer (A) crosslinked. Specific examples of the epihalohydrins are epichlorohydrin, epibromohydrin, etc.

(3) Compounds having two or more epoxy groups; the two or more epoxy groups in this compound react respectively with two or more amino or imino groups, crosslinking the polymer (A). Specific examples of the compound are diglycidylethers such as 1,4-butanediol diglycidylether, 1,2-ethanediol diglycidylether, bisphenol A diglycidylether, etc.

(4) Compounds having two or more isocyanate groups; the two isocyanate groups in this compound react respectively with two or more amino or imino groups, crosslinking the polymer (A). Specific examples of the compound are tolylene diisocyanate, diphenylmethane diisocyanate, etc.

(5) Compounds having two or more acid chloride groups; the acid chloride groups react respectively with the amino or imino groups. Specific examples of the compounds are succinyl dichloride, etc. Additionally, acryloyl chloride reacts with the amino or imino groups at the acid chloride portion and also at the acryloyl portion in the Michael addition reaction.

(6) Compounds having two or more carboxylic ester groups or tetrabasic acid dianhydrides; the carboxylic ester groups or acid anhydride groups react with amino or imino groups forming amide bonds. Specific examples of the compound are saturated carboxylic alkylesters such as dimethyl succinate, dimethyl malonate, etc., and tetrabasic acid dianhydrides such as pyromellitic dianhydride, etc, or the like.

(7) Dihalogenated hydrocarbons; the compounds react with amino or imino groups forming ammonium salts. Specific examples are 1,3-dichloropropane, 1,2-dichloroethane, 1,3-dibromopropane, 1,2-dibromoethane, etc.

The condition for the crosslinking reaction of polymer (A) with the above compound (B) may be selected adequately according to the kinds of the polymer (A) and the compound (B). For example, since the reactions of epihalohydrins with amino or imino groups proceed very rapidly, a reaction in the absence of a solvent is preferably carried out at around 0° C., the Michael addition reaction is at room temperature (25° C.) level, and the amide-bond forming reaction is preferably conducted under heating. The reaction period is not limited but usually about 1 to 100 hours. The reaction product is, after converted to a salt if desired by e.g., neutralization in an aqueous hydrochloric acid solution, dried by the method well known in the art to yield a crosslinked anion exchange resin (in the salt form). The dried resins may be further crushed according to the application thereof.

It was found that it was difficult to obtain a crosslinked anion exchange resin or a salt thereof having the water absorption ratio of 4.0 or less when the crosslinking reaction of the polymer (A) with the compound (B) as crosslinking agent was conducted in a solvent mainly containing water especially when the compound (B) reactive to water was used, and that the crosslinking reaction was preferably conducted in the absence of a solvent or in the presence of a nonaqueous solvent. From this viewpoint, the present invention includes a phosphorus adsorbent using a crosslinked anion exchange resin or a salt thereof that is prepared by the crosslinking reaction of polymer (A) with compound (B) in the absence of a solvent or in the presence of a nonaqueous solvent.

In the case where a polymer liquid at room temperature such as polyethyleneimine or the like is used as the polymer (A), the solvent is not required and thus the crosslinking reaction is preferably conducted in the absence of a solvent. In the case where a polymer highly viscous or solid at ordinary temperature is used as the polymer (A), the crosslinking reaction described above may be conducted using a nonaqueous solvent as needed. The nonaqueous solvent means a solvent having 3 mass % or less water therein. When a solvent containing water beyond 3 mass % is used, it becomes difficult to obtain the desired degree of crosslinking, due to the reactions with water of functional groups in, e.g., the compounds containing epoxy groups such as epihalohydrins, diglycidylethers, the compounds containing isocyanate groups or the like.

As the solvent may be used a solvent that does not participate in the crosslinking reaction and can solubilize the polymer (A) and the compound (B) providing a homogeneous reaction environment, or a solvent that does not solubilize but disperse the polymer (A) and the compound (B) providing an heterogeneous reaction environment. Specific examples of the former solvent include lower alcohols such as methanol, ethanol, isopropanol, etc., ethers such as tetrahydrofuran, 1,4-dioxane, isopropylether, etc., aromatic hydrocarbon solvents such as benzene, toluene, etc., and so on when methyl acrylate is used as the compound (B), and ethers such as tetrahydrofuran, 1,4-dioxane, isopropylether, etc., aromatic hydrocarbon solvents such as benzene, toluene, etc., and so on when epichlorohydrin is used as the compound (B). The latter solvent may be properly selected according to the kind of the compound (B), and specific examples thereof are aliphatic or alicyclic hydrocarbon solvents such as n-hexane, cyclohexane, heptane, etc., when epichlorohydrin is used as the compound (B).

Compound (B) used as a crosslinking agent may be preferably added in an amount properly selected so that the crosslinked anion exchange resin or the salt thereof obtained has the water absorption ratio of 4.0 or less. The amount is also carefully selected for providing the crosslinked resin or the salt thereof with a desired phosphorus adsorption capacity and the selective adsorption property to phosphorus. Water absorption ratio of the present invention is a value determined by the steps consisting of enclosing a predetermined amount of an anion exchange resin sample in a porous container such as a non-woven fabric bag, immersing the container in pure water for 24 hours, dehydrating the container at 1300 rpm for 3 minutes in a centrifuge, the mass of the sample being measured, the mass after water absorption being divided by the mass before water absorption, and the value thus obtained being further subtracted by 1.

A crosslinked anion exchange resin or a salt thereof having the water absorption ratio beyond 4.0 cannot have a high level of phosphorus adsorption capacity and phosphorus selective adsorption property. Therefore, the upper limit of the water absorption ratio is set at 4.0 in the present invention. The lower limit thereof is not particularly limited and may be at 0. The polymer (A) of the present invention is a hydrophilic polymer having amino or imino groups, and thus a low water absorption ratio indicates a high degree of crosslinking. The reason for increases in the phosphorus adsorption capacity and the phosphorus selective adsorption associated with an increase in the degree of crosslinking is not clear, but it is contemplated that the crosslinking and the hydrogen bonding by the compound (B) combined confine the resin into a considerably dense three dimensional structure and phosphorus adsorbed therein is securely contained in the three dimensional network, and that the lattices formed by the three dimensional network are sufficiently large for penetration of phosphate ions, but not for penetration of higher molecular weight organic acids such as glycocholic acid.

The upper limit of the water absorption ratio is preferably 3.8, more preferably, 3.6, 3.4, 3.0 in the order, and most preferably 2.8. While, the lower limit thereof is preferably 0.1, more preferably 0.2, and most preferably 0.4.

In order to make the water absorption ratio 4.0 or less, the compound (B) is preferably used in an amount of 2 to 50 mol % with respect to total moles of the amino or imino groups in the polymer (A). With the compound (B) being used in an amount of less than 2 mol %, the resulting polymer may have the water absorption ratio of more than 4.0, and may not have the desired phosphorus adsorption capacity due to insufficient crosslinking. Even when the compound (B) having two or more functional groups is added in an amount of 50 mol % in a reaction system, there still remain amino or imino groups left that are not involved in the crosslinking reaction, as are usually found in general chemical reactions. Further, amino or imino groups involved in the Michael addition reaction provide secondary and/or tertiary amines that are still capable of ion exchanging. Therefore, the upper limit of the compound (B) to be added is set as 50 mol %. The upper limit of the compound (B) to be used is more preferably 40 mol % or less with respect to total moles of the amino or imino groups in the polymer (A), more preferably 30 mol % or less, and particularly preferably 25 mol % or less.

The crosslinked anion exchange resin of the present invention may be used as an anion exchange resin containing the amino or imino groups as they are in the free base form. Additionally, the crosslinked anion exchange resin may be converted to a salt thereof. Example of the salt include salts of inorganic acids such as hydrochloric acid, sulfuric acid, bicarbonic acid, carbonic acid, nitric acid, phosphoric acid (not favorable when used as a phosphorus adsorbent), etc.; organic acids containing a carboxyl group (s) such as oxalic acid, tartaric acid, benzoic acid, p-methoxybenzoic acid, p-hydroxybenzoic acid, valeric acid, citric acid, glyoxylic acid, glycolic acid, glyceric acid, glutaric acid, chloroacetic acid, chloropropionic acid, cinnamic acid, succinic acid, acetic acid, lactic acid, pyruvic acid, fumaric acid, propionic acid, 3-hydroxypropionic acid, malonic acid, butyric acid, isobutyric acid, amino acids, imidinoacetic acid, malic acid, isethionic acid, citraconic acid, adipic acid, itaconic acid, crotonic acid, salicylic acid, gluconic acid, glucuronic acid, gallic acid, sorbic acid, etc.; and organic acids containing a sulfonic acid group such as sulfoacetic acid, methanesulfonic acid, ethanesulfonic acid, etc. The crosslinked anion exchange resin may also be partially chelated.

Particularly when used in the medical application, the crosslinked anion exchange resin should be converted to a pharmaceutically acceptable salt, and thus salts including halides; inorganic acids salts such as hydrochloride, sulfate, bicarbonate, carbonate, etc.; organic acids such as formate, acetate, propionate, malonate, succinate, fumalate, ascorbate, glucuronate, aspartate, amino acid salts such as glutamate, etc., are recommended. Among them, a halide ion as the counter ion, in particular chloride ion, is favorable since the crosslinked anion exchange resin has the highest phosphate adsorption capacity when it has a chloride ion.

The crosslinked anion exchange resin or the salt thereof of the present invention (hereinafter, referred to solely as the "crosslinked anion exchange resin") may be used in all areas where the weak basic anion exchange resins known in the art are utilized. Additionally, the crosslinked anion exchange resin of the present invention is extremely useful as a phosphorus adsorbent since it has an excellent phosphorus adsorption capacity.

The crosslinked anion exchange resin of the present invention has an excellent phosphate-ion adsorbing capacity, and thus may be used, in industrial applications, for removal of phosphate ions in water of lakes, lagoons, and rivers, or in wastewater. In this case, the crosslinked anion exchange resin may be used as it is or attached on a support known in the art, as the phosphorus adsorbent. Specific purification methods include, for example, a method by filling the crosslinked anion exchange resins in a treatment tank and subsequently introducing liquid to be treated therein, and a method to sink a porous container such as a bag filled with the anion exchange resins in lakes, lagoons or the like to be treated. Additionally, the crosslinked anion exchange resins may be used in combination with other phosphorus adsorbents or other adsorbents, and in such a case, the crosslinked anion exchange resin is preferably contained in the phosphorus adsorbent of the present invention in an amount of 0.1 mass % or more from a viewpoint of the phosphorus adsorption property. The phosphorus adsorbent of the present invention can be also used for removal of phosphorus in food during food processing, and may be applied for soil improvement.

The phosphorus adsorbent of the present invention can also be used in the medicinal application and is extremely useful particularly as a preventive and therapeutic agent of hyperphosphatemia for renal failure patients. Namely when the phosphorus adsorbent comprising the crosslinked anion exchange resin of the present invention is administered as a medicine to a patient, though the anion exchange resins in the medicine are conveyed through the gastrointestinal tract and finally excreted, the crosslinked anion exchange resins adsorb and trap phosphate ions contained in food ingested by the patient during the transport in the gastrointestinal tract, suppressing the uptake and accumulation of phosphorus in the body, consequently leading to a decrease in phosphorus concentration in the blood of the patient. Additionally, the resin itself is unchanged during the aforementioned process except that the resin exerts the phosphorus adsorption action, and thus does not lead to adverse reactions of the conventional oral phosphorus adsorbents, such as aluminum preparations and the like.

Furthermore, the crosslinked anion exchange resin of the present invention has a high selectivity to phosphate ions and a low adsorption capacity to organic acids derived from cholesterol such as glycocholic acid or the like contained in the bile acids secreted from the bile duct into the small intestine. Therefore, the crosslinked anion exchange resin does not have an inconvenience in that the resin loses part of its inherent phosphorus adsorption capacity by adsorbing glycocholic acid, and retains and exerts its excellent phosphorus adsorption action. Additionally, the crosslinked anion exchange resin is extremely favorable as a medicinal phosphorus adsorbent since the resin does not show, by adsorbing glycocholic acid, an adverse effect to decrease unnecessarily blood cholesterol values in renal failure or other patients.

The crosslinked anion exchange resin of the present invention may be used as it is as a medicinal phosphorus adsorbent, in particular as an effective ingredient of a preventive and/or therapeutic agent of hyperphosphatemia, but is preferably blended with other common pharmaceutical additives into a formulation by the process well known in the art. The pharmaceutical formulations include tablets, capsules, granules, powders, pills, troches, liquids, etc., and are orally administered.

The medicinal composition for oral administration can be formulated according to the processes well known in the art, for example, by blending, filling, tabletting, etc. Additionally, the effective ingredient may be dispersed by repeated blending operations into a medicinal composition containing a large amount of fillers. For example, tablets or capsules for oral administration are preferably provided as a unit medicine, and may contain pharmaceutical supports commonly used, such as binders, fillers, diluents, tabletting agents, lubricants, disintegrants, coloring agents, flavoring agents and wetting agents, etc. The tablets may be, for example, coated with a coating agent into coat tablets according to the process well known in the art.

Preferable examples of the filler include cellulose, mannitol, lactose, etc., and disintegrants such as starch, polyvinylpyrrolidone, starch derivatives such as sodium starch glycolate, etc., or the like, and lubricants such as sodium laurylsulfate, etc., may be also used as the additives for the pharmaceutical formulations.

As liquid formulations are provided medicinal compositions of, for example, aqueous or oil-based suspension, solution, emulsion, syrup, elixir, etc, or as dried medicines are provided medicinal compositions that can be redissolved before use in water or an adequate solvent. To the liquid formulation may be added the additives well known in the art, including precipitation inhibitors such as sorbitol, syrup, methylcellulose, gelatin, hydroxyethylcellulose, carboxymethylcellulose, aluminum stearate gel, hydrogenated edible fat, etc.; emulsifiers such as lecithin, sorbitan monooleate, gum acacia, etc.; oily esters such as almond oil, rectified coconut oil (including edible oil), glycerin esters, etc.; nonaqueous solvents such as propionglycol (sic), ethyl alcohol, etc.; and preservation agents such as p-hydroxybenzoic methylester, sorbic acid, etc., as well as flavor agents or coloring agents known in the art if desired.

In formulations containing the medicinal composition for oral administration above, for example, in tablets, capsules, granules, powder, etc., the crosslinked anion exchange resin is usually contained in an amount of 5 to 95 mass %, preferably in an amount of 25 to 90 mass %. The medicinal phosphorus adsorbent of the present invention is particularly useful for prevention and/or treatment of hyperphosphatemia derived from diseases associated with renal function disorders, and in particular for prevention and treatment of hyperphosphatemia accompanied with renal function disorders. The dosage of the preventive and/or therapeutic agent may be properly determined according to the age, health condition, weight, degree of disease, kind and frequency of the other therapies and treatments concomitantly proceeding, nature of the desired effect, etc., of the patient. The dosage is generally 1 to 60 g as an effective ingredient per adult a day, and the medicine is recommended to be administered once or several times divided a day.

The preventive and/or therapeutic agent of hyperphosphatemia of the present invention decreases a phosphorus concentration in blood, and thus an amount of phosphorus excretion into urine. Accordingly, it is anticipated that the preventive and/or therapeutic agent of the present invention is effective for prevention and/or treatment, not only of hyperphosphatemia, but of renal function disorders, chronic renal failure, dialysis, hypocalcemia, excessive secretion of parathyroid hormone (PTH), suppression of vitamin D activation, ectopic calcification, etc., which are thought to have hyperphosphatemia as the cause of the disease.

Furthermore, it is also anticipated that the preventive and/or therapeutic agent of the present invention is effective for prevention and treatment of PTH increase caused by hyperphosphatemia, secondary hyperparathyroidism accompanied with a decline in vitamin D, renal bone dysplasia, uremia, central and periphery neuropathy, anemia, myocardial failure, hyperlipemia, glucose metabolism abnormality, itching disease, skin ischemic ulcer, anemia, tendon laceration, sexual dysfunction, muscular disorder, growth delay, cardiac conduction disturbance, pulmonary diffusion disturbance, arteriosclerosis, immune deficiency, etc.

EXAMPLE

Hereinafter, the present invention will be described in more detail referring to EXAMPLES, but the following EXAMPLES are not intended to limit the present invention and all modifications within a range of the scope of the present invention are embraced in the present invention. Meanwhile, crosslinked anion exchange resins were prepared according to the methods described below. Physical properties such as number averaged molecular weight and the like were obtained referring to the product catalogues of Nippon Shokubai Co., Ltd. Additionally, calcium carbonate described in the Pharmacopoeia of Japan was used.

Experimental Example 1 (Preparative Example 1)

Into a 500 ml separable flask containing 100.0 g of polyethyleneimine ("EPOMIN SP-006"; number averaged molecular weight 600; amine value 20 mg eq/g-polymer; Nippon Shokubai Co., Ltd.) was added dropwise while stirring at 30° C. under a nitrogen atmosphere, 17.7 g of methyl acrylate (8.8 mol % with respect to the total moles of amino groups and/or imino groups in polyethyleneimine) over a period of 3 hours (mainly the Michael addition reaction proceeded). After the dropwise addition, the mixture was heated to 70° C. and stirred for 2.5 hours to promote the reaction (an amide-bond forming reaction). After confirming the mixture being gelated (by the progress of crosslinking), the mixture was cooled to 30° C. and cured at the same temperature for 15 hours. The mixture was separated from the separable flask and cured for additional 1 month at room temperature.

The crosslinked anion exchange resin thus obtained was crushed and poured into 778 ml of 3N aqueous hydrochloric acid solution and the resulting mixture was stirred for 24 hours. The crosslinked anion exchange resin hydrochloride obtained was collected by filtration. The filtered resin was washed repeatedly with water and then poured into 10 L of water, and the mixture was stirred for 24 hours. The filtered resin was collected by filtration and lyophilized to yield crosslinked anion exchange resin No. 1.

Experimental Example 2 (Preparative Example 2)

According to the procedure described in EXPERIMENTAL EXAMPLE 1 except that 44.3 g of methyl acrylate (22.1 mol % with respect to the total moles of amino groups and/or imino groups in the following polyethyleneimine) was added dropwise into a 500 ml separable flask containing 100.0 g of polyethyleneimine same as that used in EXPERIMENTAL EXAMPLE 1, "EPOMIN SP-006", the Michael addition, amide-bond forming and curing reactions were conducted. The crosslinked anion exchange resin thus obtained was crushed and poured into 664 ml of 3N aqueous hydrochloric acid solution and the resulting mixture was stirred for 24 hours. The crosslinked anion exchange resin hydrochloride obtained was collected by filtration. The filtered resin was washed repeatedly with water, and then poured into 10 L of water and the mixture was stirred for 24 hours. The filtered resin was collected by filtration and lyophilized to yield crosslinked anion exchange resin No. 2.

Experimental Example 3 (Prepartive Example 3)

Into a 500 ml separable flask containing 50.0 g of polyethyleneimine ("EPOMIN SP-018"; number averaged molecular weight 1800; amine value 19 mg eq/g-polymer; Nippon Shokubai Co., Ltd.), was added, dropwise while stirring at 2° C. or lower under a nitrogen atmosphere, 10.8 g of epichlorohydrin (10.0 mol % with respect to the total moles of amino groups and/or imino groups in polyethyleneimine), and the mixture was stirred for additional 2 hours. After the stirring was terminated, the mixture was heated to 30° C. and reacted for 1.5 hours and at 50° C. for additional 1 hour. After confirming the mixture being gelated, the mixture was further heated to 60° C. and reacted for additional 1 hour. After the reaction was completed, the mixture was cured at 70° C. for 24 hours. The crosslinked anion exchange resin thus obtained was crushed and poured into 384 ml of 3N aqueous hydrochloric acid solution and the resulting mixture was stirred for 24 hours. The crosslinked anion exchange resin hydrochloride obtained was collected by filtration. The filtered resin was washed repeatedly with water and then poured into 10 L of water and the mixture was stirred for 24 hours. The filtered resin was collected by filtration and lyophilized to yield crosslinked anion exchange resin No. 3.

Experimental Example 4 (Preparative Example 4)

Into a 500 ml separable flask containing 50.0 g of polyethyleneimine ("EPOMIN SP-018") was added, while stirring at 2° C. or below under a nitrogen atmosphere, 16.1 g of epichlorohydrin (15.0 mol % with respect to the total moles of amino groups and/or imino groups in polyethyleneimine) and the mixture was stirred for 4 hours. After the stirring was terminated, the mixture was heated to 30° C. and reacted for 1.5 hours and at 50° C. for additional 1 hour. After confirming the mixture being gelated, the mixture was further heated to 60° C. and reacted for additional 1 hour. After the reaction was completed, the mixture was cured at 70° C. for 24 hours. The crosslinked anion exchange resin thus obtained was crushed and poured into 362 ml of 3N aqueous hydrochloric acid solution and the resulting mixture was stirred for 24 hours. The crosslinked anion exchange resin hydrochloride obtained was collected by filtration. The filtered resin was washed repeatedly with water, and then poured into 10 L of water and the mixture was stirred for 24 hours. The filtered resin was collected by filtration and lyophilized to yield crosslinked anion exchange resin No. 4.

Experimental Example 5 (Preparative Example 5)

Into a 500 ml separable flask containing 50.0 g of polyethyleneimine, "EPOMIN SP-006", was added, while stirring at 2° C. or lower under a nitrogen atmosphere, 16.1 g of epichlorohydrin (15.0 mol % with respect to the total moles of amino groups and/or imino groups in polyethyleneimine) and the mixture was reacted for 3.5 hours. The mixture was heated to 30° C. and reacted for 1 hour and then at 50° C. for additional 2 hours. After confirming the mixture being gelated, the stirring was terminated and the mixture was heated 60° C. and further reacted for 1 hour. After the reaction was completed, the mixture was separated from the flask and cured at 70° C. in a hot-air drier for 24 hours. The crosslinked anion exchange resin thus obtained was crushed and poured into 362 ml of 3N aqueous hydrochloric acid solution and the resulting mixture was stirred for 24 hours. The crosslinked anion exchange resin hydrochloride obtained was collected by filtration. The filtered resin was washed repeatedly with water, and then poured into 10 L of water and the mixture was stirred for 24 hours. The filtered resin was collected by filtration and lyophilized to yield crosslinked anion exchange resin No. 5.

Experimental Example 6 (Preparative Example 6)

Into a 500 ml separable flask containing 50.0 g of polyethyleneimine ("EPOMIN SP-200"; number averaged molecular weight 10,000; amine value 18 mg eq/g-polymer; Nippon Shokubai Co., Ltd.) was added dropwise while stirring at 50° C. under a nitrogen atmosphere, 11.6 g of ethyl acrylate over a period of 0.5 hour. After the dropwise addition, the mixture was reacted at 50° C. until it became solidified. After confirming the mixture being solidified, the mixture was further heated to 60° C. and reacted for additional 1 hour. After the reaction was completed, the mixture was cured at room temperature for 72 hours. The reaction product (5 g) was poured into 100 ml of 0.36N aqueous hydrochloric acid solution, and the resulting mixture was stirred for 24 hours and filtered. The filtered solid was rinsed in 400 ml of water, filtered and lyophilized to yield crosslinked anion exchange resin No. 6.

Experimental Example 7 (COMPARATIVE PREPARATIVE EXAMPLE 1)

Into a 500 ml separable flask containing 50.0 g of polyethyleneimine, "EPOMIN SP-018" and 113.5 g of water was added dropwise while stirring at 30° C. under a nitrogen atmosphere, 10.8 g of epichlorohydrin (10.0 mol % with respect to the total moles of amino groups and/or imino groups in polyethyleneimine) over a period of 10 minutes. After the dropwise addition, the mixture was reacted for 0.5 hour. After confirming the mixture being gelated, stirring was terminated and the. mixture was heated to 60° C. and reacted for additional 1 hour. After the reaction was completed, the mixture was separated from the flask and cured at 70° C. in a hot-air drier for 24 hours. The crosslinked anion exchange resin thus obtained was crushed and poured into 384 ml of 3N aqueous hydrochloric acid solution, and the mixture was stirred for 24 hours. The crosslinked anion exchange resin hydrochloride obtained was collected by filtration. The filtered resin was washed repeatedly with water, and then poured into 10 L of water and the mixture was stirred for 24 hours. The filtered resin was collected by filtration and lyophilized to yield crosslinked anion exchange resin No. 7 for comparison.

Experimental Example 8 (Comparative Preparative Example 2)

Into a 500 ml separable flask containing 50.0 g of polyethyleneimine "EPOMIN SP-018" and 195.3 g of water was added dropwise while stirring at 30° C. under a nitrogen atmosphere, 16.1 g of epichlorohydrin (15 mol % with respect to the total moles of amino groups and/or imino groups in polyethyleneimine) over a period of 15 minutes. After the dropwise addition, the mixture was reacted for 1 hour, and further at 60° C. for 10 minutes. After confirming the mixture being gelated, stirring was terminated and the mixture was reacted for additional 1 hour. After the reaction was completed, the mixture was separated from the flask and cured at 70° C. in a hot-air drier for 24 hours. The crosslinked anion exchange resin thus obtained was crushed and poured into 362 ml of 3N aqueous hydrochloric acid solution, and the mixture was stirred for 24 hours. The crosslinked anion exchange resin hydrochloride obtained was collected by filtration. The filtered resin was washed repeatedly with water, and then poured into 10 L of water and the mixture was stirred for 24 hours. The filtered resin was collected by filtration and lyophilized to yield crosslinked anion exchange resin No. 8 for comparison.

Experimental Example 9 (Comparative Preparative Example 3)

Into a 500 ml separable flask containing 25.0 g polyethyleneimine, "EPOMIN SP-018" and 155.7 g of water, was added dropwise while stirring at 30° C. under a nitrogen atmosphere, 11.9 g of epichlorohydrin (22.1 mol % with respect to the total moles of amino groups and/or imino groups in polyethyleneimine) over a period of 15 minutes. After the dropwise addition, the mixture was reacted for 0.5 hour and at 40° C. for 0.5 hour, and further heated to 60° C. and reacted for additional 15 minutes. After confirming the mixture being gelated, stirring was terminated and the mixture was reacted for additional 1 hour. After the reaction was completed, the mixture was separated from the flask and cured at 70° C. in a hot-air drier for 24 hours. The crosslinked anion exchange resin thus obtained was crushed and poured into 166 ml of 3N aqueous hydrochloric acid solution, and the mixture was stirred for 24 hours. The crosslinked anion exchange resin hydrochloride obtained was collected by filtration. The filtered resin was washed repeatedly with water, and then poured into 10 L of water and the mixture was stirred for 24 hours. The filtered resin was collected by filtration and lyophilized to yield crosslinked anion exchange resin No. 9 for comparison.

Experimental Example 10 (Comparative Preparative Example 4)

Into a 500 ml separable flask containing 25.0 g of polyethyleneimine, "EPOMIN SP-018", and 220.3 g of water was added dropwise while stirring at 30° C. under a nitrogen atmosphere, 16.1 g of epichlorohydrin (30 mol % with respect to the total moles of amino groups and/or imino groups in polyethyleneimine) over a period of 15 minutes. After the dropwise addition, the mixture was reacted for 0.75 hour and at 50° C. for 1 hour, and heated further to 60° C. and reacted for additional 20 minutes. After confirming the mixture being gelated, stirring was terminated and the mixture was reacted for additional 1 hour. After the reaction was completed, the mixture was separated from the flask and cured at 70° C. in a hot-air drier for 24 hours. The crosslinked anion exchange resin thus obtained was crushed and poured into 149 ml of 3N aqueous hydrochloric acid solution, and the mixture was stirred for 24 hours. The crosslinked anion exchange resin hydrochloride obtained was collected by filtration. The filtered resin was washed repeatedly with water, and then poured into 10 L of water and the mixture was stirred for 24 hours. The filtered resin was collected by filtration and lyophilized to yield crosslinked anion exchange resin No. 10 for comparison.

Experimental Example 11
(Measurement of Water Absorption Ratio and Phosphate Ion Adsorption Property)

concentration of glycocholic acid which was not adsorbed on the resin was determined by the use of a bile acid measurement reagent (registered trademark "Total bile acid-Test Wako"; Wako Pure Chemical Ind.), and from the measured value, the amount of glycocholic acid adsorbed on each resin sample (mmol/g-resin) was calculated. The results were shown in TABLE 1.

TABLE 1

| | Polymer | Mn | Compound (A) (sic) compound and amount (mol %) | | Water absorption ratio | Phosphate adsorption (mmol/g) | Glycocholic acid adsorption (mmol/g) |
|---|---|---|---|---|---|---|---|
| No. 1 | PEI[1] | 600 | MA[2] | 8.8 | 29.63 | 0.77 | 2.33 |
| No. 2 | PEI | 600 | MA | 22.1 | 2.78 | 2.54 | 0.47 |
| No. 3 | PEI | 1800 | EC[3] | 10 | 2.12 | 2.76 | 1.34 |
| No. 4 | PEI | 1800 | EC | 15 | 1.19 | 2.98 | 0.11 |
| No. 5 | PEI | 600 | EC | 15 | 2.29 | 2.56 | 1.78 |
| No. 6 | PEI | 10000 | EA[4] | 10 | 0.82 | 3.55 | 0.19 |
| No. 7 | PEI | 1800 | EC[5] | 10 | 15.04 | 1.76 | 2.55 |
| No. 8 | PEI | 1800 | EC[5] | 15 | 14.11 | 1.58 | 2.53 |
| No. 9 | PEI | 1800 | EC[5] | 22.1 | 9.05 | 1.3 | 2.53 |
| No. 10 | PEI | 1800 | EC[5] | 30 | 4.67 | 1.02 | 2.45 |

[1]PEI: Polyethyleneimine
[2]MA: Methyl acrylate
[3]EC: Epichlorohydrin
[4]EA: Ethyl acrylate
[5]Comparative example wherein crosslinking was conducted in aq. Solution Water absorption ratios of the crosslinked anion exchange resins hydrochloride obtained in EXPERIMENTAL EXAMPLES 1 to 10 were determined. The measurement of the water absorption ratio was conducted as follows. Samples used for the measurement were previously converted completely to their hydrochloride salts respectively. A content of nonvolatile material (a mass %) in each resin sample was determined previously. A resin sample (approximately 0.2 g) was weighed accurately (mass b), and placed in a small bag made of nonwoven fabric. The bag was heat-sealed and immersed in pure water for 24 hours (at room temperature). Subsequently, the bag was withdrawn from water and dehydrated by centrifugation at 1300 rpm for 3 minute in a centrifuge. The dehydrated bag containing the resin was weighed to yield a mass c. From the mass c of the bag containing the resin was subtracted the mass (0.47 g) of the nonwoven fabric bag, and the resulting difference was divided by the mass before water absorption (a×b), and further subtracted by 1 to yield the water absorption ratio. The compositions of respective resin samples and the results of the water absorption ratio measurement were summarized in TABLE 1.

The phosphate ion adsorption property was measured in the presence of glycocholic acid, and the adsorption capacity and the selectivity were evaluated. In regard to an ion concentration in the intestinal solution, each resin sample was added at a concentration of 1 mg/ml into a solution of 5 mM $NaH_2PO_4$ and 5 mM glycocholic acid, and the resulting mixture was adjusted to pH 6.8 by the addition of sodium hydroxide and stirred at 37° C. for 1 hour. Subsequently, the resin was removed by filtration through an ultrafiltration membrane, and the concentration of phosphate ions in the filtrate that were not adsorbed on the resin was determined by the use of an inorganic phosphorus measuring reagent (registered trademark "P-Test Wako"; Wako Pure Chemical Ind.). From the measured value, the amount of phosphorus adsorbed on the crosslinked anion exchange resin (mmol/g-resin) was calculated. Simultaneously, the As it may be apparent from TABLE 1, EXAMPLES 7 to 10 wherein the crosslinking reactions were conducted in aqueous solutions gave the crosslinked resins with higher water absorption ratios even though the compound (B) was used in larger amounts. The difference in the water absorption ratios is more distinguishable when the values of No. 3 (EXAMPLE of the present invention) and No. 7 (COMPARATIVE EXAMPLE) both of which have same composition, or of No. 4 (EXAMPLE of the present invention) and No. 8 (COMPARATIVE EXAMPLE) were compared. Further, even when the compound (B) was added in a significantly higher amount in Nos. 9 and 10, the water absorption ratios did not become 4.0 or less.

Figure 1:
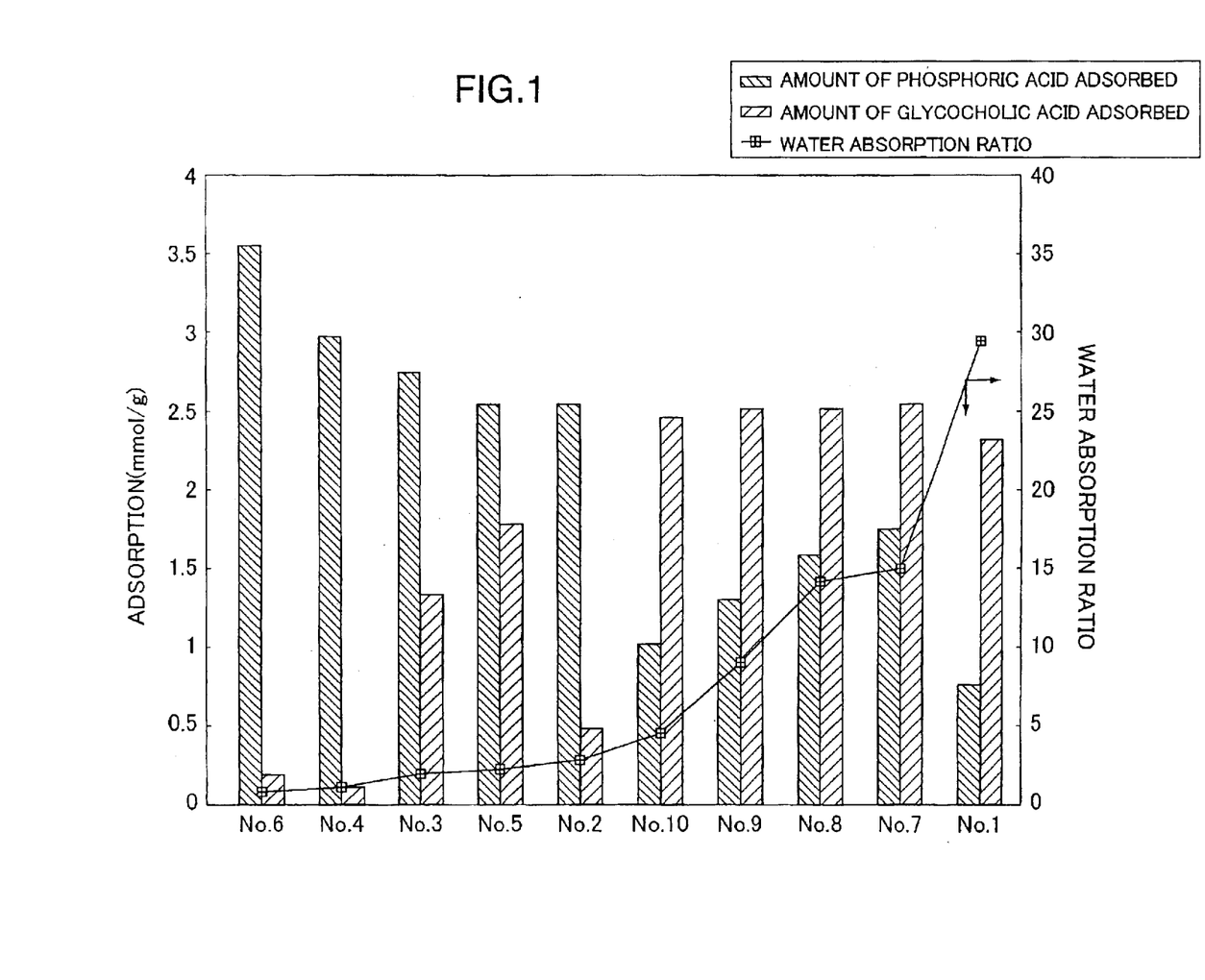
FIG. 1 is a bar graph showing the results of measurement of adsorption properties and water absorption ratio determined in EXPERIMENTAL EXAMPLE 11.

To examine the phosphate adsorption capacity and phosphorus selectivity, i.e., which of glycocholic acid or phosphoric acid is adsorbed more strongly, the values in TABLE 1 were redrawn in a bar graph (see, FIG. 1). In FIG. 1, the vertical line on the left side corresponds to the amounts of phosphoric acid (left bar in each sample) and glycocholic acid (right bar) adsorbed, while the vertical line on the right side corresponds to the water absorption ratios shown in the sequential line. In FIG. 1, the resin samples were arranged in an increasing order of the water absorption ratio from left. As it may be apparent from FIG. 1, the resin sample No. 6 having the lowest water absorption ratio has the highest phosphate ion adsorption capacity while adsorbs almost no glycocholic acid, indicating the resin is extremely excellent in the phosphorus selectivity. It was also confirmed that the resins having the water absorption ratio beyond 4.0 adsorb more glycocholic acid than phosphoric acid, and thus were not within the scope of the present invention.

Figure 2:
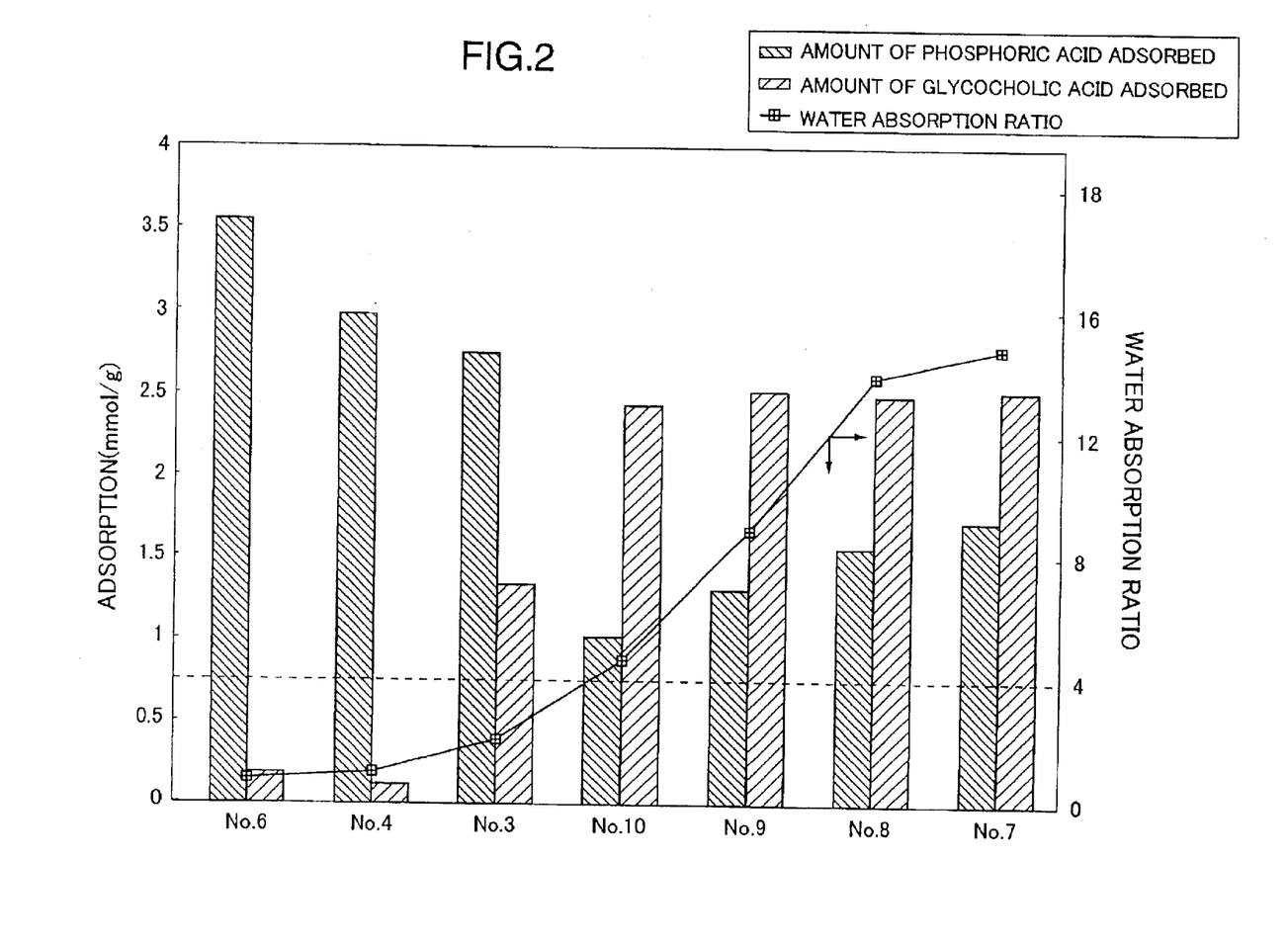
FIG. 2 is a bar graph showing a part of the results in FIG. 1.

Additionally, the results from the resin samples prepared from polyethyleneimines having molecular weight of 1800 and 10000 were redrawn as a graph in FIG. 2, similarly to FIG. 1. The graph shows more clearly the correlation between the water absorption ratio and the phosphorus selectivity.

Experimental Example 12 (Preparative Example 7)

Into a 500 ml separable flask containing 50.0 g of polyethyleneimine ("EPOMIN SP-018") was added dropwise while stirring at 40° C. under a nitrogen atmosphere, 12.5 g of methyl acrylate (12.5 mol % with respect to the total moles of amino groups and/or imino groups in polyethyleneimine) over a period of 1.5 hours. After the dropwise addition, the mixture was heated to 70° C. and reacted for 2.5 hours. After confirming the mixture being gelated, the mixture was cured at 70° C. for additional 72 hours. The crosslinked anion exchange resin thus obtained was crushed and poured into 373 ml of 3N aqueous hydrochloric acid solution, and the mixture was stirred for 24 hours. The crosslinked anion exchange resin hydrochloride obtained was collected by filtration. The filtered resin was washed repeatedly with water, and then poured into 10 L of water and the mixture was stirred for 24 hours. The filtered resin was collected by filtration and lyophilized to yield crosslinked anion exchange resin No. 11.

Experimental Example 13 (Preparative Example 8)

According to the method of EXPERIMENTAL EXAMPLE 12 except that into a 500 ml separable flask containing 50.0 g of polyethyleneimine, "EPOMIN SP-018" was added 15.0 g of methyl acrylate (15.0 mol % with respect to the total moles of amino groups and/or imino groups in polyethyleneimine), crosslinked anion exchange resin No. 12 was obtained.

Experimental Example 14 (Preparative Example 9)

According to the method of EXPERIMENTAL EXAMPLE 12 except that into a 500 ml separable flask containing 50.0 g of polyethyleneimine, "EPOMIN SP-018", was added 17.5 g of methyl acrylate (17.5 mol % with respect to the total moles of amino groups and/or imino groups in polyethyleneimine), crosslinked anion exchange resin No. 13 was obtained.

Experimental Example 15 (Preparative Example 10)

Into a 500 ml separable flask containing 50.0 g of polyethyleneimine ("EPOMIN SP-200"; number averaged molecular weight 10,000; amine value 18 mg eq/g-polymer; Nippon Shokubai Co., Ltd.) was added dropwise while stirring at 50° C. under a nitrogen atmosphere, 10.0 g of methylacrylate (10 mol % with respect to the total moles of amino groups and/or imino groups in polyethyleneimine) over a period of 1 hour. After the dropwise addition, the mixture was heated to 70° C. and reacted for 2.5 hour, and after confirming the mixture being gelated, the mixture was cured at 70° C. for additional 72 hours. The crosslinked anion exchange resin thus obtained was crushed and poured into 405 ml of 3N aqueous hydrochloric acid solution, and the mixture was stirred for 24 hours. The crosslinked anion exchange resin hydrochloride obtained was collected by filtration. The filtered resin was washed repeatedly with water, and then poured into 10 L of water and the mixture was stirred for 24 hours. The filtered resin was collected by filtration and lyophilized to yield crosslinked anion exchange resin No. 14.

Experimental Example 16 (Preparative Example 11)

Into a 500 ml separable flask containing 50.0 g of polyethyleneimine, ("EPOMIN SP-200") was added dropwise while stirring at 50° C. under a nitrogen atmosphere, 15.0 g of methyl acrylate (1 mol % with respect to the total moles of amino groups and/or imino groups in polyethyleneimine) over a period of 1.5 hours. After the dropwise addition, the mixture was heated to 70° C. and reacted for 2.5 hours and after confirming the mixture being gelated, the mixture was cured at 70° C. for additional 72 hours. The crosslinked anion exchange resin thus obtained was crushed and poured into 362 ml of 3N aqueous hydrochloric acid solution, and the mixture was stirred for 24 hours. The crosslinked anion exchange resin hydrochloride obtained was collected by filtration. The filtered resin was washed repeatedly with water, and then poured into 10 L of water and the mixture was stirred for 24 hours. The filtered resin was collected by filtration and lyophilized to yield crosslinked anion exchange resin No. 15.

Experimental Example 17
(Measurement of Phosphate Ion Adsorption at Ion Concentration in Intestinal Solution)

Figure 3:
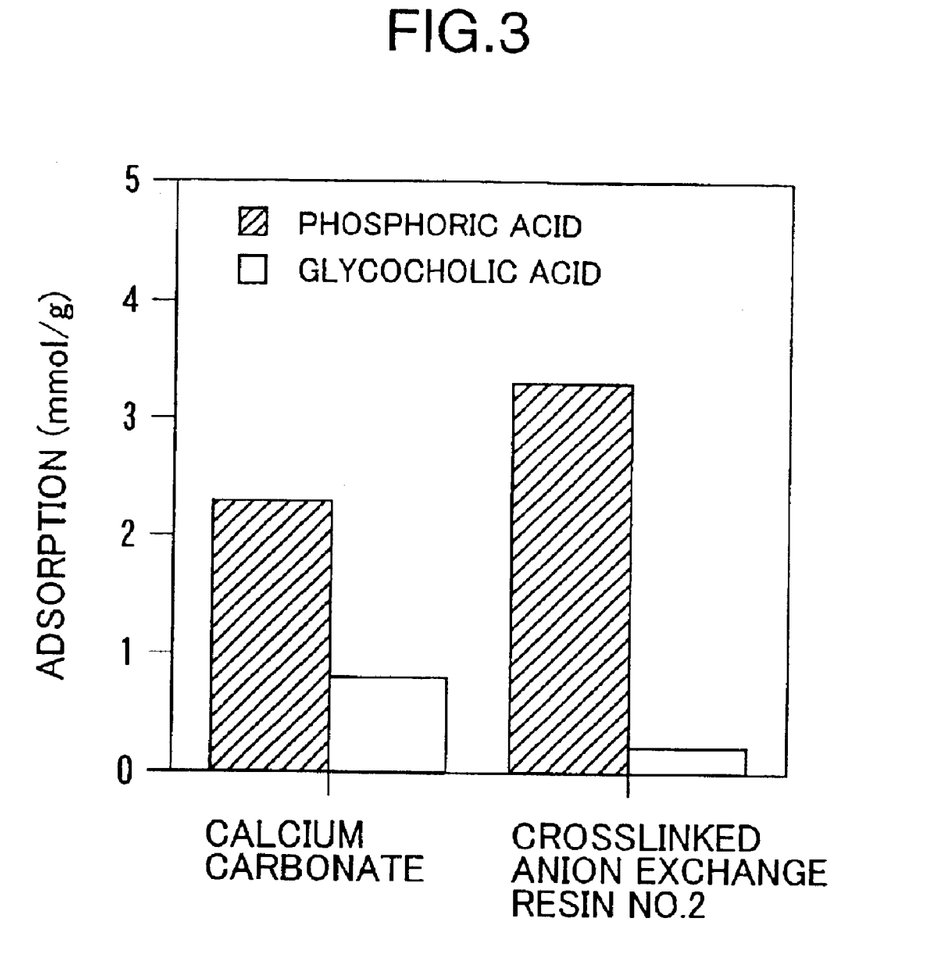
FIG. 3 is a bar graph showing the results of measurement of adsorption properties determined in EXPERIMENTAL EXAMPLE 17.

Phosphate ion adsorption properties of calcium carbonate that has been used as a medicinal oral phosphorus adsorbent and a crosslinked anion exchange resin of the present invention in the presence of glycocholic acid were examined. In regard to an ion concentration in the intestinal solution, crosslinked anion exchange resin No. 2 obtained EXPERIMENTAL EXAMPLE 2 and calcium carbonate were added respectively in solutions of 5 mM $NaH_2PO_4$ and 5 mM glycocholic acid at a concentration of 1 mg/ml, and the resulting mixtures were adjusted to pH 6.8 by the addition of sodium hydroxide and stirred at 37° C. for 1 hour. Subsequently, the resin was removed by filtration through a filter, and the amount of phosphoric acid that was not adsorbed on the resin was determined by the use of an inorganic phosphorus-measuring reagent (registered trademark "P-Test Wako"; Wako Pure Chemical Ind.). From the measured value, the amount of phosphorus adsorbed on the crosslinked anion exchange resin sample (mmol/g-resin) was calculated. Simultaneously, the amount of glycocholic acid which was not adsorbed on the resin was determined by the use of a bile acid measurement reagent (registered trademark "Total bile acid-Test Wako"; Wako Pure Chemical Ind.), and from the measured value, the amount of glycocholic acid adsorbed on the resin sample (mmol/g resin) was calculated. The results were shown in FIG. 3.

It is apparent that crosslinked anion exchange resin No. 2 has a larger phosphoric acid adsorption capacity than calcium carbonate and a extremely low absorption capacity of glycocholic acid Experimental Example 18
(Effects on Phosphorus Amount in Blood and Urine of Normal Rats)

Suppressive effects of crosslinked anion exchange resin No. 2 and calcium carbonate to the increase in a phosphorus amount in urine have been examined using male SD rats (8 weeks old). First, feedstuff containing 0.3 mass % of phosphorus (20 g/rat/day) was fed for 7 days. Subsequently, the feedstuff containing 0.58 mass % of phosphorus (20 g/rat/day) was blended with 0.6 g of crosslinked anion exchange resin No. 2 obtained in EXPERIMENTAL EXAMPLE 2 or calcium carbonate, and the mixed feedstuff was administered for 5 days.

Before and 5 days after the first administration, urine for 24 hours was collected and the phosphorus amount in the urine was calculated from the concentration of phosphorus and the volume of urine. The phosphorus concentration in urine was determined by the use of an inorganic phosphorus-measurement reagent (registered trademark "P-test Wako"; Wako Pure Chemical Ind.).

From the differences in the phosphorus amount before and 5 days after the first administration, urinary phosphorus excretions (increases in phosphorus excretion into urine [mg/24 hours]) were calculated and compared with those of the non-administered group (control). Meanwhile, 6 rats are used in each group.

Figure 4:
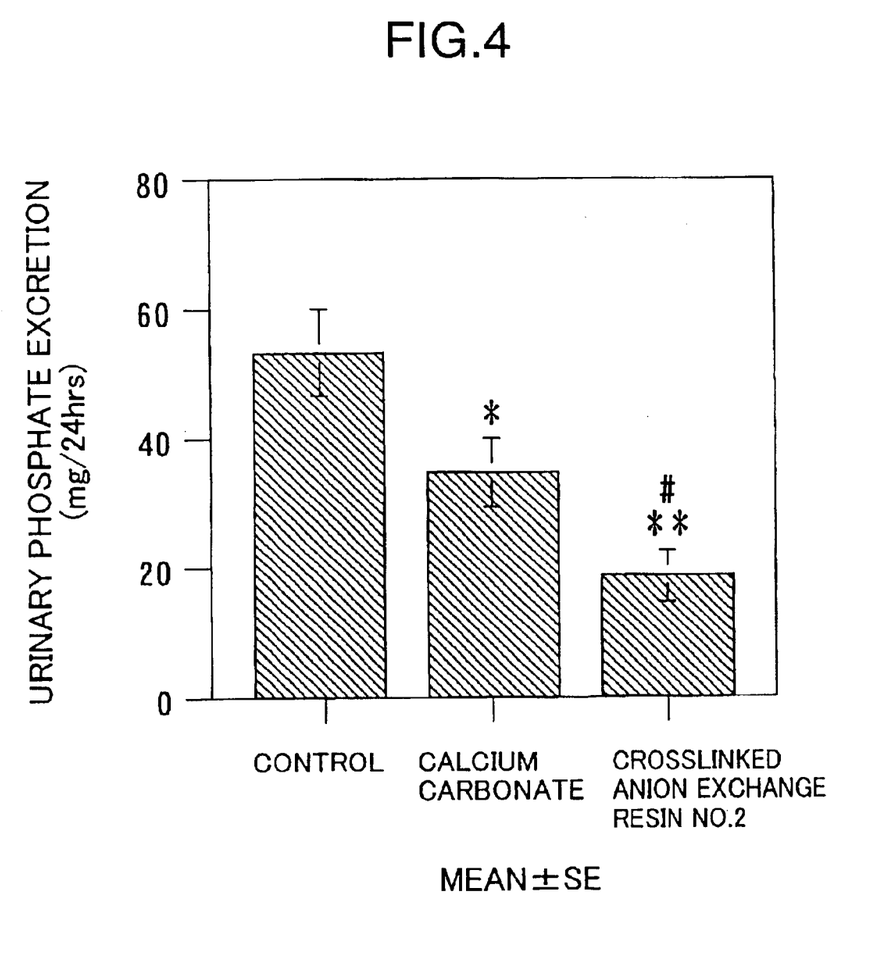
FIG. 4 is a bar graph showing the results of measurement of increase in phosphorus excreted in urine determined in EXPERIMENTAL EXAMPLE 18.

The results are shown in FIG. 4. The increase of urinary phosphorus excretion was suppressed with a statistically significant difference in the calcium carbonate-administered group, compared to the control group. In the group administered with the crosslinked anion exchange resin was also statistically suppressed the increase of urinary phosphorus excretion, and the effect was greatly larger than that in the calcium carbonate-administered group. Meanwhile in the FIGURE, * and ** indicate that the group has a significant difference from the control (respectively, P<0.05 and P<0.01 in Student's T-Test). Additionally, # indicates that the group has a significant difference from the calcium carbonate-administered group (P<0.05 and P<0.01, Student's T-Test).

Experimental Example 19
(Effects on Phosphorus Concentration in Blood and Renal Function of 5/6 Nephrectomized Rats)

The effects of crosslinked anion exchange resin and calcium carbonate on the suppressive action on phosphorus amount in urine and on renal functions were examined using male SD rats (9 weeks old). First, ⅔ of the left kidneys of male SD rats and after a week, all of the right kidneys thereof were removed to give 5/6 nephrectomized rats. After 1 week, feedstuff blended with calcium carbonate or crosslinked anion exchange resin No. 2 obtained in EXPERIMENTAL EXAMPLE 2 was administered. As the powdery feedstuff for rats was used MF manufactured by Oriental Yeast Co. Ltd., and the dosage was 15 g of the feedstuff containing 0.3 g of calcium carbonate and crosslinked anion exchange resin No. 2, respectively. After 12 weeks from the day the 5/6 nephrectomized rats were obtained, blood samples were withdrawn from the tail veins of the rats, and the phosphorus concentrations in blood were determined by an inorganic-measurement reagent (P-Test, Wako, mentioned above). Additionally, before and after 12 weeks from the day the 5/6 nephrectomized rats were prepared, urines were collected respectively for 24 hours, and protein concentrations in the urines were determined by a protein measurement reagent (Protein Assay Kit, Bio-Rad). Meanwhile, the number of rats in each group used for experiment was 9 respectively.

Figure 5:
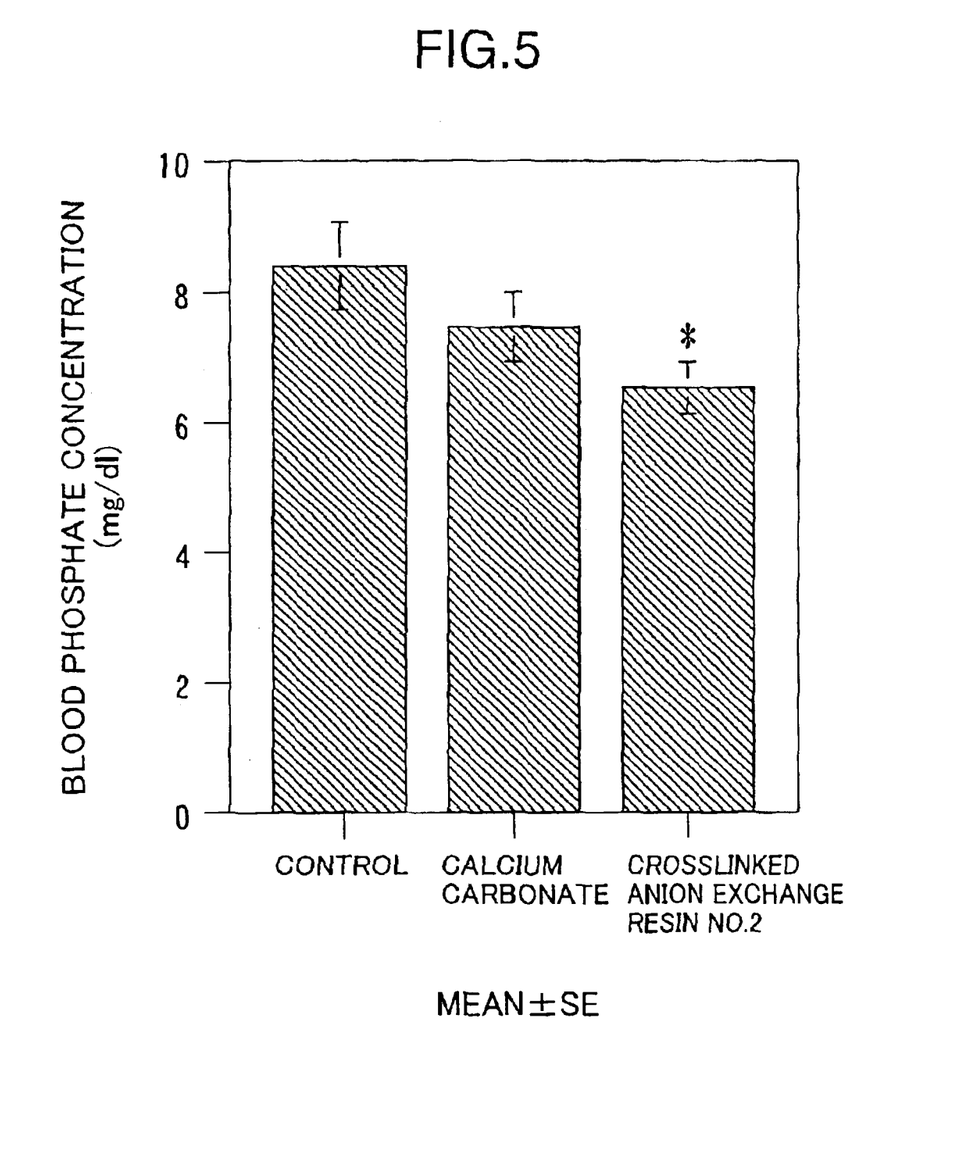
FIG. 5 is a bar graph showing the results of phosphorus concentration in blood determined in EXPERIMENTAL EXAMPLE 19.
Figure 6:
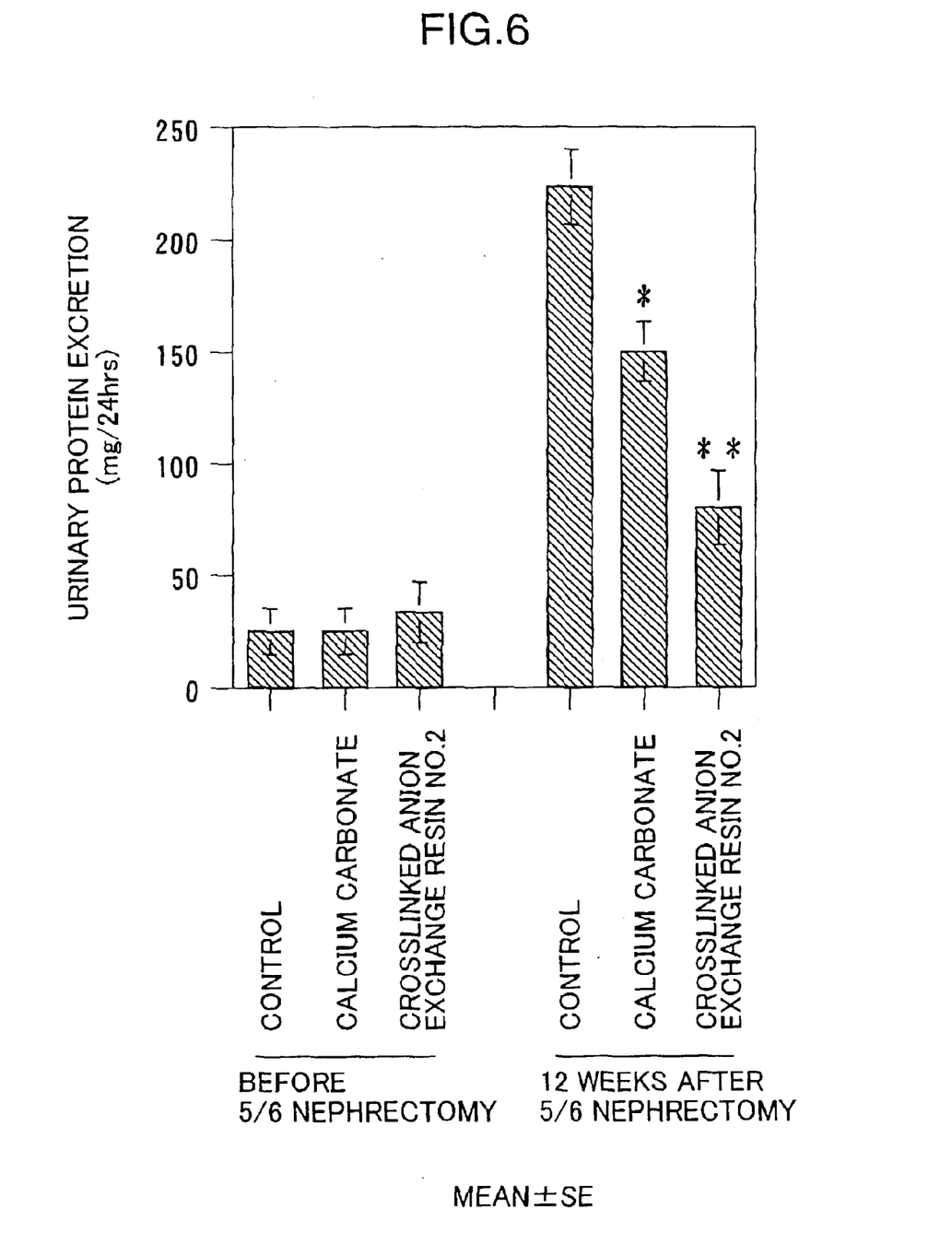
FIG. 6 is a bar graph showing the results of protein excretion into urine determined in EXPERIMENTAL EXAMPLE 19.

The results were shown in FIG. 5 and FIG. 6. As shown in FIG. 5, the calcium carbonate-administered group did not have a statistically significant difference in blood phosphorus concentration, compared to the control. But, the group administered with crosslinked anion exchange resin No. 2 had a significant decrease in blood phosphorus concentration. On the other hand as shown in FIG. 6, after 12 weeks from preparation of the 5/6 nephrectomized rats, a marked increase in protein excretion into urine was observed in the control, indicating the deterioration of renal function, while the increase in protein excretion into urine was significantly suppressed in the calcium carbonate administered group compared to the control. In the group administered with crosslinked anion exchange resin No. 2, the increase in protein excretion into urine was also significantly suppressed, and the effect was greater than that of the calcium carbonated-administered group indicating an excellent suppressive effect thereof to the deterioration of renal function.

INDUSTRIAL APPLICABILITY

A crosslinked anion exchange resin or a salt thereof of the present invention is excellent in its phosphorus adsorption capacity and thus can be used as a phosphorus adsorbent for purification of water in ponds, lagoons and the like. Further, it adsorbs efficiently phosphorus in a selective manner even in the presence of glycocholic acid or the like in the gastrointestinal tracts, and thus could decrease markedly a phosphorus concentration in blood and a phosphorus excretion into urine, consequently suppressing deterioration of renal functions. Therefore, the crosslinked anion exchange resin or the salt thereof of the present invention is also useful as a medicinal phosphorus adsorbent, and as a preventive and therapeutic agent of hyperphosphatemia.

What is claimed is:

1. A crosslinked anion exchange resin or a salt thereof obtained by reacting a polymer (A) having amino and/or imino groups in the total number of two or more per molecule with a compound (B) having vinyl groups capable of the Michael addition reaction with amino and/or imino groups contained in the polymer (A) and carboxylic ester groups capable of reacting with amino and/or imino groups contained in the polymer (A), and by having a water absorption ratio of 4.0 or less.

2. The crosslinked anion exchange resin or a salt thereof according to claim 1, wherein said crosslinked anion exchange resin or a salt thereof is obtained by reacting said polymer (A) with said compound (B) in the absence of a solvent or in the presence of a non aqueous solvent.

3. The crosslinked anion exchange resin or a salt thereof according to claim 1, wherein said polymer (A) has a number averaged molecular weight of 200 or more.

4. The crosslinked anion exchange resin or a salt thereof according to claim 1, wherein said polymer (A) is one or more polymer selected from the group consisting of polyalkyleneimine, polyallylamine, polyvinylamine and allylamine-vinylamine copolymer.

5. The crosslinked anion exchange resin or a salt thereof according to claim 3, wherein said polymer (A) is one or more polymer selected from the group consisting of polyalkyleneimine, polyallylamine, polyvinylamine and allylamine-vinylamine copolymer.

6. The crosslinked anion exchange resin or a salt thereof according to claim 1, wherein the total amount of the amino and/or imino groups of said polymer (A) is 8 to 67 mg eq/g defined by an amine value per gram of said polymer (A).

7. The crosslinked anion exchange resin or a salt thereof according to claim 1, wherein said compound (B) is used in an amount of 2 to 50 mol % with respect to total moles of the amino or imino groups in said polymer (A).

8. The crosslinked anion exchange resin or a salt thereof according to claim 1, wherein said compound (B) is one or more esters selected from the group consisting of (meth) acrylic esters, fumaric mono- or diesters, maleic mono- or diesters, and itaconic mono- or diesters, each of said esters having ester groups including alkyl esters having 1 to 10 carbon atoms, cycloalkylesters and benzylesters.

* * * * *

UNITED STATES PATENT AND TRADEMARK OFFICE
CERTIFICATE OF CORRECTION

PATENT NO.    : 6,844,372 B2
DATED         : January 18, 2005
INVENTOR(S)   : Takeshi Goto et al.

It is certified that error appears in the above-identified patent and that said Letters Patent is hereby corrected as shown below:

Title page,
Item [73], Assignees, please correct "Hisamitsu Pharmaceutical Co., Inc. (Saga, Japan)" to -- Hisamitsu Pharmaceutical Co., Inc. (Saga, Japan) and Nippon Shokubai Co., Ltd. (Osaka, Japan) --.

Signed and Sealed this

Twenty-second Day of March, 2005

JON W. DUDAS
*Director of the United States Patent and Trademark Office*